United States Patent [19]

Nachbur et al.

[11] 4,059,532

[45] Nov. 22, 1977

[54] PHOSPHORUS-CONTAINING REACTION PRODUCTS USEFUL AS FLAMEPROOFING AGENTS

[75] Inventors: Hermann Nachbur, Dornach; Peter Rohringer, Basel, both of Switzerland

[73] Assignee: Ciba-Geigy Corporation, Ardsley, N.Y.

[21] Appl. No.: 638,140

[22] Filed: Dec. 5, 1975

[30] Foreign Application Priority Data

Dec. 9, 1974 Switzerland ..................... 16311/74
Feb. 12, 1975 Switzerland ..................... 1716/75

[51] Int. Cl.² ............................................... C09K 3/00
[52] U.S. Cl. ............................ 252/8.1; 106/15 FP; 260/DIG. 24
[58] Field of Search ............... 252/8.1; 106/15 FP; 260/DIG. 24

[56] References Cited

U.S. PATENT DOCUMENTS 3,877,952  4/1975  Dahmen et al. ................. 252/8.1 X

*Primary Examiner*—Stephen J. Lechert, Jr.
*Attorney, Agent, or Firm*—Edward McC. Roberts; Prabodh I. Almaula

[57] ABSTRACT

Phosphorus-containing reaction products are provided which are formed from:
a. an amidophosphate of the formula

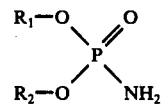

in which $R_1$ and $R_2$ each are lower alkyl, halogenoalkyl or alkenyl or $R_1$ and $R_2$ together are lower alkylene;
b. a 1,3,5-triazine substituted by at least 2 primary amino groups;
c. formaldehyde and, optionally,
d. a lower alkanol.

These phosphorus-containing reaction products are useful as flameproofing agents for cellulose-containing fiber materials.

15 Claims, No Drawings

PHOSPHORUS-CONTAINING REACTION PRODUCTS USEFUL AS FLAMEPROOFING AGENTS

The invention relates to phosphorus-containing reaction products formed from a. 2 to 6 moles of an amidophosphate of the formula

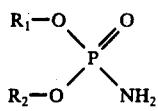 (1)

wherein $R_1$ and $R_2$ each independently represent alkyl having 1 to 4 carbon atoms, halogenoalkyl or alkenyl having 2 to 4 carbon atoms, or $R_1$ and $R_2$ together stand for alkylene having 2 to 5, preferably 2 to 4 carbon atoms;

b. 1 mole of a 1,3,5-triazine substituted by at least 2 primary amino groups;

c. 2 to 12 moles of formaldehyde or of an agent releasing formaldehyde; and d. 0 to 6 moles of an alkanol having 1 to 4 carbon atoms.

The constituents (a), (b) and (c) are all simultaneously reacted in the process, or firstly (a) with (c) and afterwards with (b), or firstly (b) with (c) and afterwards with (a), or firstly (b) with (c), thereupon with (a) and subsequently again with (c).

The phosphorus-containing reaction product is preferably composed of 2 to 6, especially 4 to 6, moles of the constituent (a), 1 mole of the constituent (b), 2 to 6 moles of the constituent (c) and 0 to 5 moles of the constituent (d).

Further likewise preferred reaction products are composed of 2 to 5 moles of the constituent (a), 1 mole of the constituent (b), 2 to 6, preferably 2 to 5, moles of constituent (c) and 0 to 5, preferably 0 to 3, moles of the constituent (d).

The radicals $R_1$ and $R_2$ in the formula (1) can be different from each other or, preferably, identical. It is also possible that the reaction products contain radicals of more than one compound of the formula (1). That is to say, the phosphorus-containing reaction products can be composed of compounds of the formula (1) that are different from each other.

$R_1$ and $R_2$ can represent, e.g., 2-chloroethyl, 2,3-dichloropropyl, 2,3-dibromopropyl or allyl, especially n-butyl, sec.butyl or methyl, preferably isopropyl and, in particular, ethyl.

Furthermore, $R_1$ and $R_2$ can together represent unbranched or preferably branched-chain alkylene, such as ethylene, n-propylene, 1-methyl-n-propylene or, in particular, 2,2-dimethyl-propylene.

Preferably, however, $R_1$ and $R_2$ represent alkyl radicals having 1 to 4, especially 1 to 3, carbon atoms.

Accordingly, preferred amidophosphates correspond as constituent (a) to the formula

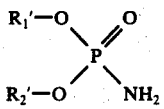 (2)

wherein $R_1'$ and $R_2'$ in each case stand for alkyl having 1 to 4 carbon atoms, or together for alkylene having 2 to 4 carbon atoms; and in particular to the formula

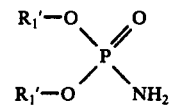 (3)

wherein $R_1'$ has the given meanings. Particularly suitable amidophosphates are O,O'-dialkylamidophosphates of the formula

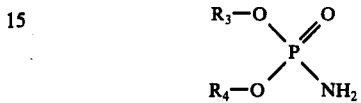 (4)

and especially those of the formula

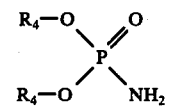 (5)

wherein $R_3$ and $R_4$ each stand for alkyl having 1 to 4 carbon atoms.

As examples of specific compounds for the constituent (a), there may be mentioned the compounds of the formulae

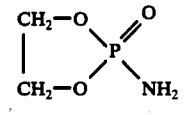 (6.1.)

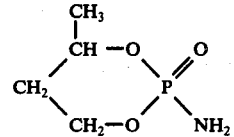 (6.2.)

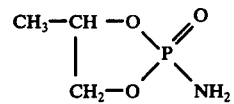 (6.3)

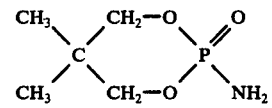 (6.4.), also di-isopropyl- and, in particular, diethyl-O,O'-amidophosphate.

Suitable as constituent (b) or as 1,3,5-triazines are, e.g., acetoguanamine, formoguanimine, benzoguanamine or, in particular, melamine.

In the case of constituent (c), this is preferably formaldehyde itself, or an agent releasing formaldehyde, such as paraformaldehyde.

The constituent (d) is preferably not used. It may however be desirable to use in some cases products of which the free methylol groups are etherified. Suitable as etherification constituent (d) are in this case, e.g., n-butanol, n-propanol, isobutanol, especially ethanol or, in particular, methanol.

The phosphorus-containing reaction products of the invention do not as a rule have a uniform structure, but have in most cases various proportions of higher and lower condensed products. The average molecular weight of the reaction products is as a rule between 400 and 3000, particularly between 1000 and 3000.

As already mentioned, the phosphorus-containing reaction products can be obtained by reaction of the different constituents in various sequences. Preferred products are however those wherein the constituents (b) and (c) have been preliminarily reacted with each other, i.e. products that have been obtained from the constituent (a) and an already methylolated 1,3,5-aminotriazine substituted by at least two primary amino groups, especially a melamine methylolated with 5 to 6 methylol groups. The preferred products thus obtained can also be in the after-methylolated and, optionally, after-etherified form, whereby in the case of after-methylolation 3 to 6 moles of formaldehyde per mole of constituent (a) have been used.

Preferred phosphorus-containing reaction products correspond probably to the formula

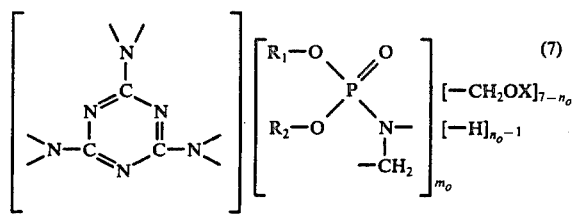

wherein $R_1$ and $R_2$ have the given meanings, X represents hydrogen or alkyl having 1 to 4 carbon atoms, $m_o$ represents an integer from 2 to 6, and $n_o$ represents an integer from 1 to 7; and in particular they correspond to the formula

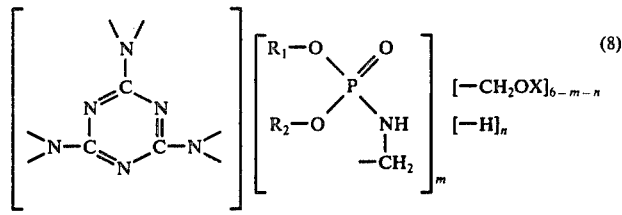

wherein $R_1$, $R_2$ and X have the given meanings, m represents an integer from 2 to 6, especially 4 to 6, and n represents at most 6-m; n is therefore 0 or an integer from 1 to 4, depending on the value of m.

Of particular interest are also phosphorus-containing reaction products of the probable formula

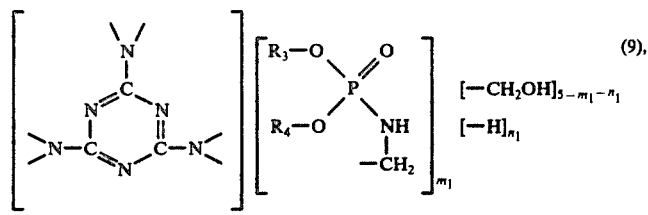

wherein $R_3$ and $R_4$ each stand for alkyl having 1 to 4 carbon atoms, $m_1$ represents an integer from 2 to 5 and $n_1$ represents at most 5-$m_1$; $n_1$ is therefore 0, 1, 2, or 3, depending on the value of $m_1$.

Especially suitable however are phosphorus-containing reaction products of the probable formula

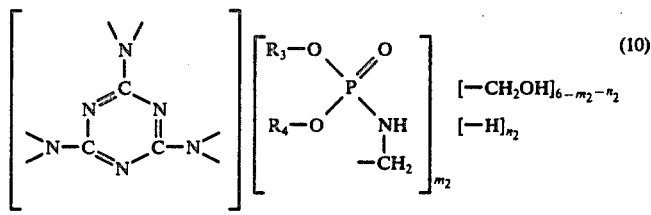

wherein $R_3$ and $R_4$ have the given meanings, $m_2$ represents an integer from 4 to 6 and $n_2$ represents at most 6-$m_2$; $n_2$ is therefore 0, 1 or 2 depending on the value of $m_2$.

The phosphorus-containing reaction product of the probable formula

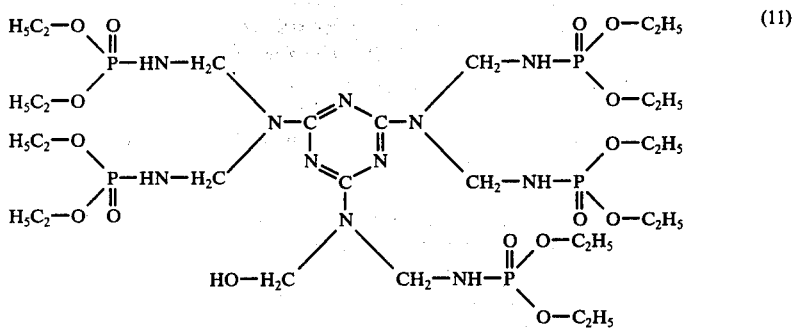

has proved to be particularly advantageous.

The dialkylamidophosphate radicals in the formulae (7) to (11) are bound with a methylene carbon atom, which comes from the formaldehyde, to a nitrogen atom of the aminotriazine. The —CH$_2$—O— radicals are bound with the carbon atom to a nitrogen atom either of the triazine radical or of a dialkylamidophosphate radical. The radicals X are bound solely to oxygen atoms of —CH$_2$—O— groups, whilst the hydrogen atoms are bound to a nitrogen atom of the triazine radical or of a dialkylamidophosphate radical.

Depending on what value $m_o$ and $n_o$ have in the formula (7), there are formed reaction products having from 2 to 6 amidophosphate radicals and from 0 to 6 methylol groups, which can, if necessary, be partially or completely etherified.

Analogues can be stated for formulae (8), (9) and (10) with the indices $m$, $m_1$, $m_2$, $n$, $n_1$ and $n_2$.

The phosphorus-containing reaction products according to the invention can be produced by conventional methods known per se. An advantageous procedure is to react the constituents (a), (b) and (c) with each other at a temperature of 70° to 180° C. All three constituents are simultaneously reacted together in the so-called single-vessel process, or firstly the constituent (a) is reacted with the constituent (c) and subsequently with the constituent (b), or preferably firstly (b) is reacted with (c) and subsequently with (a), or firstly (b) is reacted with (c), thereupon with (a) and subsequently again with (c). If necessary, it is possible at the end to etherify any free methylol groups with the constituent (d).

To 1 mole of the constituent (b) there are used in the process 2 to 6 moles of the constituent (a), 2 to 12 moles of the constituent (c) and 0 to 6 moles of the constituent (d). In a preferred embodiment there are used per mole of the constituent (b) 2 to 6 moles, preferably 4 to 6 moles, of the constituent (a), 2 to 6 moles of the constituent (c) and 0 to 5 moles of the constituent (d). In a further likewise preferred embodiment there are used per mole of the constituent (b) 2 to 5 moles of the constituent (a), 2 to 6 moles, preferably 3 to 5 moles, of the constituent (c) and 0 to 5 moles, preferably 0 to 3 moles, of the constituent (d). The reaction of the methylol compound of the constituent (a) with unmethylolated constituent (b), or preferably of the methylol compound of the constituent (b) with unmethylolated constituent (a), is performed preferably in an anhydrous medium.

The phosphorus-containing reaction products can if required be also after-methylolated at the end.

Before and/or preferably after the after-methylolation, it is possible to perform also etherification with an alkanol having 1 to 4 carbon atoms.

The methylolation reactions, i.e. the methylolation of one of the constituents (a) or (b) or the after-methylolation are performed advantageously at temperatures of up to 150° C, preferably at 50° to 100° C. This reaction is optionally carried out in the presence of a basic catalyst, with suitable such catalysts being both strong bases, such as sodium hydroxide or potassium hydroxide, and weak bases, such as sodium acetate, magnesium carbonate or magnesium oxide.

The degree of methylolation can be ascertained by determination of the bound formaldehyde.

Etherified, phosphorus-containing reaction products are obtained by complete or partial etherification of the methylol groups with a monovalent aliphatic alcohol containing at most 4 carbon atoms in the presence of an acid.

The actual production of the phosphorus-containing reaction products is carried out advantageously by condensation of a compound of the formula (1) with a 1,3,5-triazine containing at least two primary amino groups, whereby at least one H$_2$N-group of one of these two starting constituents must be methylolated, with heating, preferably in an anhydrous medium, e.g. in the presence of an organic solvent which forms with water an azeotrope, such as benzene, toluene or xylene. The reaction temperature is between 70° and 180° C, preferably between 70° and 140° C.

The water formed during the reaction can be removed completely or only partially from the reaction mixture by, e.g., distillation. With only partial removal of the water, the reaction time can be shortened, with as a rule less higher-molecular proportions of condensation product being formed. Too large proportions of higher-molecular condensation products can have a disadvantageous effect on the handle of fibre materials finished with these products. Although the water is not completely removed, the reaction occurs practically quantitatively; the condensation to higher-molecular condensation products is, however, greatly reduced.

Furthermore, it is also possible to carry out the condensation reaction without the use of a solvent in the melt. In this case, the melamine derivative is added, e.g., to the melt of the amidophosphate. The condensation temperature for this procedure is preferably 90° to 120° C and the condensation time is 60 to 5 minutes, especially 30 to 10 minutes.

The condensation products of the invention produced in this manner are soluble in cold water. For the purpose of better handling, they can if required be dissolved in water directly before their application as fireproofing agents, and buffered, e.g., with tertiary sodium phosphate to a pH-value of 5 to 8.

The preferred products mentioned for the synthesis of the phosphorus-containing reaction products according to the invention are used in a corresponding manner also in production.

The phosphorus-containing reaction products are suitable, in particular, for use as effective and permanent fireproofing agents for cellulose-containing fibre materials.

The cellulose or the cellulose part of the fibre material can be among others linen, synthetic silk, spun rayon or, in particular, cotton. In addition to pure cellulose fibres, suitable materials are also mixtures of fibres, such as polyester/cellulose or polyamide/cellulose. The fibre materials are, e.g., wood, paper or, preferably, textiles in any desired stage of processing, such as filaments, yarns, bobbins, fleeces, knitted goods, fabrics or finished articles of clothing.

The invention relates therefore also to a process for the fireproofing of cellulose-containing fibre materials, in which process there is applied to these materials an aqueous preparation containing at least one phosphorus-containing reaction product of the defined composition; the materials are thereupon dried and then subjected to a treatment at elevated temperature.

The pH-value of the aqueous preparations containing the phosphorus-containing reaction products is advantageously less than 7.5, especially less than 5. In order to effect this, there are added to the preparations mineral acids such as sulphuric acid, nitric acid, hydrochloric acid or, preferably, phosphoric acid. Instead of using the acids themselves, especially hydrochloric acid, it is also possible to use compounds from which are readily formed in water (e.g. without heating) by hydrolysis the corresponding acids. Examples that may be mentioned here are phosphorus trichloride, phosphorus pentachloride, phosphorus oxychloride, thionyl chloride, sulphuryl chloride, acetyl chloride and chloroacetyl chloride. These compounds yield on hydrolysis solely acid cleavage products, e.g. phosphoric acid and hydrochloric acid. It can be advantageous to use, instead of one of the mentioned strong acids, the acid mixtures corresponding to the hydrolysis products of one of the aforementioned compounds.

In order to accelerate the curing process, the preparations can also contain so-called latent acid catalysts, such as ammonium chloride, ammonium dihydrogenorthophosphate, magnesium chloride, zink nitrate and others, particularly 2-amino-2-methyl-1-propanol-hydrochloride.

In addition to the phosphorus-containing reaction products and the additives necessary for the adjustment of the pH-value, the preparations for fireproofing may contain further substances.

An addition of aminoplast pre-condensates for the obtainment of a fireproofing finish that is fast to washing is particularly advantageous.

Aminoplast pre-condensates are as a rule addition products of formaldehyde with nitrogen compounds that can be methylolated. The following may be mentioned as nitrogen compounds that can be methylolated: 1,3,5-aminotriazines such as N-substituted melamines, e.g. N-butylmelamine, N-trihalogenomethylmelamines, triazones as well as guanamines, e.g. benzoguanamines, acetoguanamines or diguanamines.

Also suitable are: cyanamide, acrylamide, alkyl- or arylurea and alkyl- or arylthioureas, alkyleneureas or alkylenediureas, e.g. urea, thiourea, urones, ethylene urea, propylene urea, acetylene diurea or, in particular, 4,5-dihydroxyimidazolidone-2 and derivatives thereof, e.g. 4,5-dihydroxyimidazolidone-2 substituted in the 4-position on the hydroxyl group with the radical —$CH_2CH_2CO$—NH—$CH_2OH$. Preferably used are the methylol compounds of a urea, of an ethylene urea or, in particular, of melamine. Valuable products are yielded in general by products that are methylolated to the highest possible degree, especially however also by low-methylolated products, e.g. etherified or unetherified methylolmelamines, such as di- or trimethylolmelamine, or corresponding ethers thereof. Suitable aminoplast pre-condensates are both predominantly monomolecular aminoplasts and higher pre-condensed aminoplasts.

Also the ethers of these aminoplast pre-condensates can be used together with the reaction products. Suitable ethers are, e.g., the ethers of alkanols such as methanol, ethanol, n-propanol, isopropanol, n-butanol or pentanols.

It is advantageous, however, if these aminoplast pre-condensates are water-soluble, such as pentamethylolmelaminedimethyl ether or trimethylolmelaminedimethyl ether.

A further additive that is advantageous in some cases is a softening finishing auxiliary, e.g an aqueous polysiloxane emulsion or polyethylene emulsion or an ethylene copolymer emulsion, or especially soft-handle agents such as are described in the Belgian Patent Specification No. 808,621, e.g. the imidazole of the formula

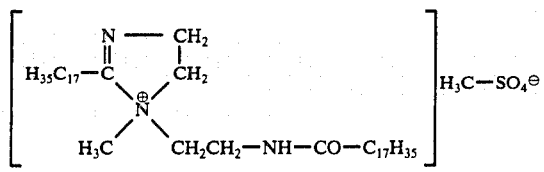

(12)

or highly etherified melamine-formaldehyde condensation products modified with fatty acid alkanolamides.

The content of phosphorus-containing reaction products in the aqueous preparations is preferably such that 10 to 28% is applied to the material to be treated. It is to be taken into account in this respect that the commercial textile materials made from untreated or regenerated cellulose are able to absorb between 50 and 120% of an aqueous preparation.

The amount of the additive that is required to obtain a pH-value of less than 7.5 is dependent on the chosen value and on the type of additive, inasmuch as it is not possible to go below a certain minimum. A certain excess above this minimum amount is generally to be recommended. Large excess amounts offer no advantage and can even prove to be harmful.

If there is added to the preparation a soft-handle agent of the given type, then the amounts added are advantageously small, e.g. 1 to 10%, relative to the amount of the phosphorus-containing reaction products.

The preparations are then applied to the cellulose-containing fibre materials, an operation that can be performed in a manner known per se. The material to be treated is preferably in the form of piece-goods and these are impregnated on a padding machine of the usual construction, which contains the preparation at room temperature.

The fibre material treated in this manner has then to be dried, the drying being advantageously carried out at a temperature of up to 100° C. It is then subjected to a dry heat treatment at a temperature of above 100° C, e.g. between 130° and 200° C, and preferably between 150° and 180° C; the higher the temperature the shorter can be the duration of the drying treatment. This time of heating is, for example, 2 to 6 minutes at a temperature of between 150° and 180° C. Since in this operation the methylol or methylol ether radicals are split in the phosphorus-containing reaction products, there is formed water or an alcohol. It has been shown that these volatile cleavage products have to be continuously removed from the material in order that the desired effect can occur to the full extent. The devices in which the heat treatment is performed are to be chosen accordingly. The equipment well suited is that in which, with maintenance of the prescribed temperature, there is a continuous supply of fresh air and a continuous removal of the air charged with the formed volatile substances.

Such devices, e.g. so-called turbo-fixers (Turbofixierer) or nozzle fixers (Dusenfixierer), are known.

A subsequent washing treatment with an acid-binding agent, preferably with aqueous sodium carbonate solution, e.g. at 40° C to boiling temperature and for 3 to 10 minutes, is advantageous in the case of a strongly acid reaction medium.

As already stated, there can be obtained by the present process fireproof finishes which are largely retained even after repeated washing or dry cleaning, and which cause no unacceptable impairment of the textile-mechanical properties, such as of the handle of the treated material. The dry-creasing angle of the material which has been rendered fireproof and fast to boiling is even improved.

Percentages and parts in the following Examples are by weight.

EXAMPLE 1

61.2 parts of hexamethylolmelamine (0.2 mole) and 153 parts of O,O'-diethylamidophosphate (1 mole) as well as 250 parts of benzene are heated to boiling. After 4 hours' boiling, the calculated amount of 18 parts of water distills off azeotropically. The boiling temperature is initially 76° C and at the end of the reaction 81° C. The reaction mixture is thereupon cooled to 20° C and the benzene-insoluble, higher-condensed parts are removed by filtration. There are obtained 21 parts of benzene-insoluble white powder.

The benzene solution is concentrated under reduced pressure. There are obtained 174 parts of a highly viscous product which is soluble in the cold state both in water and in trichloroethylene. The separation of the product by means of gel permeation chromatography (GPC) gives the following composition:
approx. 35% of condensation product of molecular weight ~1000,
approx. 25% of condensation product of molecular weight ~1400,
approx. 30% of condensation product of molecular weight >2000,
approx. 5% of O,O'-diethylamidophosphate,
approx. 5% of benzene.

For the purpose of better handling, there is prepared from the highly viscous product an 80 percent aqueous solution (P-content = 12.9%).

EXAMPLE 2

The procedure as in EXAMPLE 1 is carried out except that benzene is replaced by the identical amount of xylene (isomeric mixture).

There is obtained within 35 minutes the calculated amount of 18 parts of water. The boiling temperature is at the beginning 104° C and at the end of the reaction 127° C. The reaction mixture is then cooled to 20° C and the higher-condensed parts insoluble in xylene are removed by filtration to obtain 12.7 parts of white powder insoluble in xylene.

The xylene solution is distilled under reduced pressure.

There are obtained 179 parts of a highly viscous product which is soluble in the cold state both in water and in trichloroethylene.

Separation of the product by GPC gives the following composition:
approx. 20% of condesation product of molecular weight ~1000,
approx. 20% of condensation product of molecular weight ~1400,
approx. 40% of condensation product of molecular weight >2000,
approx. 5% of O,O'-diethylamidophosphate,
approx. 15% of xylene mixture.

For the purpose of better handling, there is prepared from the highly viscous product an 80 percent aqueous solution (P-content 12.3%).

EXAMPLE 3

76.5 parts of hexamethylolmelamine (0.25 mole) and 153 parts of O,O'-diethylamidophosphate (1 mole) as well as 175 parts of xylene (isomeric mixture) are brought to boiling. There is obtained after 15 minutes' boiling the calculated amount of 18 parts of water, which distill off azeotropically. The boiling temperature at the beginning is 97° C and at the end of the reaction 116° C. The reaction mixture is then cooled to 20° C and the higher-condensed parts insoluble in xylene are separated by filtration to obtain 11 parts of highly viscous condensate insoluble in xylene.

The xylene solution is concentrated under reduced pressure to yield 177 parts of a water-soluble, colourless, highly viscous product.

Separation of the product by means of GPC gives the following composition:
approx. 12of condensation product of mol. weight ~1000,
approx. 85% of condensation product of mol. weight >2000,
approx. 1% of O,O'-dimethylamidophosphate,
approx. 2% of xylene mixture.

For the purpose of better handling, there is prepared from the highly viscous product an 80 percent aqueous solution (P-content = 11.3%).

EXAMPLE 4

102 parts of hexamethylolmelamine (0.33 mole) and 153 parts of O,O'-diethylamidophosphate (1 mole) as well as 130 parts of xylene (isomeric mixture) are brought to boiling. There is obtained after 12 minutes boiling the calculated amount of 18 parts of water, which is distilled off azeotropically. The boiling temperature at the beginning is 99° C and at the end of the reaction 109°. The reaction mixture is then cooled to 20° C and the higher-condensed parts insoluble in xylene are separated by filtration to obtain 29.5 parts of a brittle resin insoluble in xylene.

The xylene solution is concentrated under reduced pressure.

There are obtained 194 parts of a water-soluble, colourless highly viscous product.

Separation of the product by means of GPC gives the following composition:
approx. 12% of condensation product of mol. weight ~1000,
approx. 87% of condensation product of mol. weight >2000,
approx. 1% of O,O'-diethylamidophosphate.

For the purpose of better handling, there is prepared from the highly viscous product an 80 percent aqueous solution (P-content = 11.0%).

EXAMPLE 5

51.0 parts of hexamethylolmelamine (0.166 mole) and 153 parts of O,O'-diethylamidophosphate (1 mole) as well as 170 parts of toluene are heated to boiling. There is obtained after 45 minutes' boiling the calculated amount of 18 parts of water, which is distilled off azeotropically. The boiling temperature at the beginning is 96° C and at the end of the reaction 111° C. The reaction mixture is then cooled to 20° C and the higher-condensed parts insoluble in toluene are separated by filtration to obtain 5 parts of a white powder insoluble in toluene.

The toluene solution is concentrated under reduced pressure. There are obtained 176 parts of a water-soluble, colourless, highly viscous product. The separation of the product by means of GPC gives the following composition:
approx. 3% of condensation product of mol. weight ~750,
approx. 54% of condensation product of mol. weight ~1000,
approx. 40% of condensation product of mol. weight >2000,
approx. 1% of O,O'-diethylamidophosphate,
approx. 2% of toluene.

For the purpose of better handling, there is prepared from the highly viscous product an 80 percent aqueous solution (P-content = 13.7%).

EXAMPLE 6

93 parts of the highly viscous condensation product described in Example 5 (corresponding to 0.528 mole of employed diethylamidophosphate) are dissolved in 41.6 parts of a 36% aqueous formaldehyde solution (0.5 mole) and methylolated at 60° C for 4 hours. The pH is maintained at 8-9 by the addition of, in all, 2 parts of a 30% aqueous sodium hydroxide solution. After cooling to 20° C, the content of free formaldehyde is 7.3 parts (0.23 mole). This corresponds to an approx. 50% after-methylolation or to the introduction of about 3 additional methylol groups per mole of the condensation product. Yield: 136 parts of an aqueous low-viscous product which contains 74% of active substance (P-content: 11.0%).

A portion of the low-viscous product is freed from water under reduced pressure and separated by means of GPC, from which is shown the following composition:
approx. 3% of condensation product of mol. weight ~500,
approx. 55% of condensation product of mol. weight ~1000,
approx. 39% of condensation product of mol. weight >2000,
approx. 2% of O,O'-diethylamidophosphate,
approx. 1% of toluene.

EXAMPLE 7

25.5 parts of hexamethylolmelamine (0.083 mole) and 76.5 parts of O,O'-diethylamidophosphate (0.5 mole) are heated to boiling in 170 parts of toluene with rapid stirring. There is obtained after 70 minutes' boiling the calculated amount of 9 parts of water, which distill of azeotropically. The boiling temperature at the beginning is 102° C and at the end of the reaction 108° C. The toluene is thereupon distilled off under reduced pressure to leave 93 parts of a viscous colourless product.

After the addition of 20.83 parts of a 36% aqueous formaldehyde solution (0.25 mole), this reaction product is heated to 60° C and methylolated for 3 hours at this temperature. The pH is maintained at 8.5 to 9.5 by the addition of all together 2.5 parts of a 30% aqueous sodium hydroxide solution. After cooling to 20° C, the content of free formaldehyde is 1.77 parts (0.06 mole). This corresponds to an approx. 75% after-methylolation or to the introduction of about 2.25 additional methylol groups per mole of the condensation product. Yield: 116 g of aqueous low-viscous product which contains 86.5% of active substance (P-content: 12.9%). After separation by means of GPC, the product shows the following composition:
approx. 3% of condensation product of mol. weight ~750,
approx. 52% of condensation product of mol. weight ~1000,
approx. 42% of condensation product of mol. weight >2000,
approx. 1% of O,O'-diethylamidophosphate,
approx. 2% of toluene.

EXAMPLE 8

61.2 parts of hexamethylolmelamine (0.2 mole) and 153 parts of O,O'-diethylamidophosphate (1 mole) as well as 200 parts of xylene (isomeric mixture) are heated to boiling. After 10 minutes' boiling, 9 parts of water distill off azeotropically at 104°-110° C, which corresponds to 50% of the theoretically calculated amount of water. The reaction mixture is cooled to 20° C and the xylene is removed at 60°-70° C under reduced pressure. There are obtained 190 parts of a water-soluble, highly viscous product which, after separation by means of GPC, gives the following composition:
approx. 35% of condensation product of mol. weight ~1000,
approx. 20% of condensation product of mol. weight ~1400,
approx. 35% of condensation product of mol. weight >2000,
approx. 5% of O,O'-diethylamidophosphate,
approx. 5of xylene mixture.

For the purpose of better handling, there is prepared from the highly viscous product an 80% aqueous solution, which is buffered with tertiary sodium phosphate to pH 7 and filtered off from insoluble, higher-condensed parts (P-content: 13.0%).

EXAMPLE 9

153 parts of diethylamidophosphate (1 mole) are heated to 100° C. To the clear low-viscous melt there are then added 61.2 parts of hexamethylolmelamine (0.2 mole), whereupon the temperature falls for a short time to 85° C and rises again to 110° C within 2 to 3 minutes. Condensation is now performed for 15 minutes at 110° C, with gradually a clear low-viscous product being formed. The reaction mixture is thereupon cooled to 40° C and the condensation product is filtered off from traces of undissolved parts. There are obtained 210 parts of a water-soluble, colourless, practically clear, medium-viscous condensate (P-content: 14.5%) which, after separation by means of GPC, gives the following composition:

approx. 1% of condensation product of mol. weight ~500,
approx. 9% of condensation product of mol. weight ~750,
approx. 13% of condensation product of mol. weight ~1000,
approx. 57% of condensation product of mol. weight >2000,
approx. 20% of O,O'-diethylamidophosphate.

EXAMPLE 10

61.2 parts of hexamethylolmelamine (0.2 mole) and 181 parts of O,O'-diisopropylamidophosphate (1 mole) as well as 250 parts of xylene (isomeric mixture) are heated to boiling. After 1 ½ hours' boiling, the calculated amount of 18 parts of water distills off azeotropically. The boiling temperature at the beginning is 108° C and at the end of the reaction 132° C.

After the removal of xylene under reduced pressure, there are obtained 180 parts of a water-soluble, highly-viscous product. The separation of the product by means of GPC-gives the following composition:

approx. 6% of condensation product of mol. weight ~700,
approx. 14% of condensation product of mol. weight ~1000,
approx. 72% of condensation product of mol. weight >2000,
approx. 4% of O,O'-diisopropylamidophosphate,
approx. 4% of xylene mixture.

For the purpose of better handling, there is prepared from the highly-viscous product an 80% aqueous solution (P-content: 13.5%).

EXAMPLE 11

51.2 parts of hexamethylolmelamine (0.166 mole) and 153 parts of O,0'-diethylamidophosphate (1 mole) as well as 290 parts of toluene are heated to boiling. After a boiling time of 1 hour, the calculated amount of 18 parts of water distills off azeotropically. The boiling temperature is 130° C at the beginning and 148° C at the end of the reaction. After removal of the toluene under reduced pressure there are obtained 188 parts of a viscous colourless condensation product.

After the addition of 41 parts of a 36.5% aqueous formaldehyde solution (0.5 mole), the condensation product is heated to 60° C and methylolated for 3 hours at this temperature. The pH is maintained at 8.5 to 9.5 by the addition of all together 3 parts of a 30% aqueous sodium hydroxide solution. After cooling to 20° C, the content of free formaldehyde is 1.80 parts (about 0.06 mole), which corresponds to an approx. 88% after-methylolation or to the introduction of about 2.6 additional methylol groups per mole of the condensation product. After concentration of the reaction solution under reduced pressure, there are obtained 198 g of the colourless, viscous, after-methylolated product. The after-methylolated product is dissolved in.

130 parts of methanol and etherified for 4 hours at 75° C, with the pH being maintained at 2.7 to 3.0 by the introduction of hydrochloric acid gas. The reaction mixture is subsequently neutralised to pH 7.5 by the addition of anhydrous sodium carbonate. The reaction mixture is thereupon filtered off from insoluble, higher-condensed parts and inorganic salts. There are obtained 10 parts of a white powder insoluble in methanol.

After concentration of the methanolic filtrate by evaporation, there are obtained 208 g of a water-soluble, viscous, colourless, methylolated and etherified condensation product (P-content: 14.7%).

Separation of the products by means of GPC gives the following composition:

approx. 16% of condensation product of mol. weight ~500,
approx. 9% of condensation product of mol. weight ~700,
approx. 25% of condensation product of mol. weight ~1000,
approx. 37% of condensation product of mol. weight >2000,
approx. 6.5% of O,O'-diethylamidophosphate,
approx. 6.5% of methanol and toluene.

EXAMPLE 12

30.7 parts of hexamethylolmelamine (0.1 mole) and 82.5 parts of 2,2-dimethylcyclopropyl-O,O'-amidophosphate (see formula [6.4]) (0.5 mole) as well as 286 parts of xylene (isomeric mixture) are heated to boiling. After a boiling time of half an hour, the calculated amount of 9 parts of water distills of azeotropically. The boiling temperature is 105° C at the beginning and 130° C at the end of the reaction. The reaction mixture is thereupon cooled to 20° C and the higher-condensed parts insoluble in xylene are separated by filtration. There are obtained 5 parts of a white powder insoluble in xylene.

The xylene solution is concentrated under reduced pressure. There are obtained 93 parts of a white amorphous product which is soluble in cold water. The separation of the product by means of GPC gives the following composition:

approx. 22% of condensation product of mol. weight ~400,
approx. 9% of condensation product of mol. weight ~600,
approx. 6% of condensation product of mol. weight ~700,
approx. 7% of condensation product of mol. weight ~1000,
approx. 56% of condensation product of mol. weight >2000.

For the purpose of better handling, there is prepared from the amorphous product an 80% aqueous solution (P-content: 13.0%).

EXAMPLE 13

A cotton fabric is padded with the aqueous liquors A and B given in the following Table I. The liquor absorption is 80%. The material is dried for 30 minutes at 80° C and thereupon cured for 4½ minutes at 160° C. A portion of the fabric is subsequently washed at 95° C for 5 minutes in a solution containing per litre of water 4 g of anhydrous sodium carbonate and 1 g of an addition product of 1 mole of 4-nonylphenol and 9 moles of ethylene oxide; the material is afterwards rinsed and dried.

A further portion of this fabric is now washed 20 times for 30 times in a solution at 95° C, which solution contains 2 g of anhydrous sodium carbonate and 5 g of soap per litre of water.

The individual pieces of fabric are subsequently tested with respect to their fireproofness (vertical test according to DIN 53906). The results of these tests are given in the following Table I.

Table I

|  | Untreated | Treated with liquors A | B |
|---|---|---|---|
| Constituents in g/l of liquor |  |  |  |
| product according to Example 1 |  | 290 | 290 |
| di-trimethylolmelamine |  | 120 |  |
| trimethylolmelaminedimethyl ether |  |  | 178 |
| 2-amino-2-methyl-1-propanol-hydrochloride |  | 40 | 40 |
| pH-value of the bath |  | 5,8 | 5,3 |
| degree of fixing in % |  | 62 | 75 |
| Fireproofness |  |  |  |
| BT = burning time in sec. |  |  |  |
| SL = spreading length in cm |  |  |  |

Table I-continued

|  |  | Untreated | Treated with liquors A | B |
|---|---|---|---|---|
| after subsequent washing | BT | burns | 0 | 0 |
|  | SL |  | 12,5 | 12 |
| after 20 washings | BT | burns | 0 | 0 |
|  | SL |  | 12,5 | 12 |
| handle* after subsequent washing |  | 0 | ½ | 2½ |

*Handle scale:
0 = unchanged
1 = trace stiffer than 0
2 = somewhat stiffer than 0
3 = stiff
4 = very stiff Similar results are obtained also with the product according to Example 2.

EXAMPLE 14

In a manner analogous to that described in Example 13, a cotton fabric is rendered fireproof with the liquors A to E and then tested. The results are shown in the following Table II.

Table II

|  |  | Untreated | Treated with liquors A | B | C | D | E |
|---|---|---|---|---|---|---|---|
| Constitutents in g/l of liquor |  |  |  |  |  |  |  |
| product according to Example 3 |  |  | 310 |  |  |  |  |
| product according to Example 4 |  |  |  | 340 |  |  |  |
| product according to Example 5 |  |  |  |  | 228 |  |  |
| product according to Example 6 |  |  |  |  |  | 284 |  |
| product according to Example 7 |  |  |  |  |  |  | 243 |
| 2-amino-2-methyl-1-propanol-hydrochloride |  |  | 40 | 40 | 40 | 40 | 40 |
| reaction product from 1 mole of 4-nonylphenol and 9 moles of ethylene oxide (25%) |  |  | 2 | 2 | 2 | 2 | 2 |
| di-trimethylolmelamine |  |  | 120 | 120 | 120 | 60 | 120 |
| hexamethylolmelaminepentamethyl ether-stearic acid-alkanolamide reaction product |  |  | 20 | 20 | 20 | 20 | 20 |
| pH-value of the bath |  |  | 3,9 | 5,9 | 6,9 | 6,1 | 6,6 |
| degree of fixing in % |  |  | 97 | 87 | 67 | 66 | 72 |
| Fireproofness |  |  |  |  |  |  |  |
| BT = burning time in sec. |  |  |  |  |  |  |  |
| SL = spreading length in cm. |  |  |  |  |  |  |  |
| after subsequent washing | BT | burns | 0 | 0 | 0 | 0 | 0 |
|  | SL |  | 11 | 10,5 | 12 | 13 | 11,5 |
| after 20 washings | BT | burns | 0 | 0 | 0 | 0 | 0 |
|  | SL |  | 11,5 | 11,5 | 12 | 15,5 | 11,5 |
| after 40 washings | BT | burns | 0 | 0 | — | 0 | 0 |
|  | SL |  | 12,5 | 12 | — | 13,5 | 12,5 |
| handle* after subsequent washing | (*see Table I) | 0 | 3 | 3 | ½ | ½ | 1 |

Similar results are obtained also with the products according to Example 8 or 9.

EXAMPLE 15

In a manner analogous to that described in Example 13, a cotton fabric is rendered fireproof with the liquors A to D and subsequently tested. The results are given in the following Table III.

Table III

|  |  | Untreated | Treated with liquors A | B | C | D |
|---|---|---|---|---|---|---|
| Constituents in g/l of liquor |  |  |  |  |  |  |
| product according to Example 10 |  |  | 324 | — | — | — |
| product according to Example 11 |  |  | — | 298 | 298 | — |
| product according to Example 12 |  |  | — | — | — | 377 |
| di-trimethylolmelamine |  |  | 180 | 120 | 60 | 180 |
| 2-amino-2-methyl-1-propanol-hydrochloride |  |  | 40 | 40 | 40 | 40 |
| hexamethylolmelaminepentamethyl ether-stearic acid-alkanolamide reaction product |  |  | 20 | 20 | 20 | 20 |
| pH-value of the bath |  |  | 6,1 | 6,7 | 5,5 | 5,5 |
| degree of fixing in % |  |  | 87 | 67 | 62 | 72 |
| Fireproofness |  |  |  |  |  |  |
| BT = burning time in sec. |  |  |  |  |  |  |
| SL = spreading length in cm. |  |  |  |  |  |  |
| after subsequent washing | BT | burns | 0 | 0 | 0 | 0 |
|  | SL |  | 9 | 9 | 10 | 10 |
| after 20 washings | BT | burns | 0 | 0 | 0 | 0 |
|  | SL |  | 10,5 | 10,5 | 11 | 11 |
| after 40 washings | BT | burns | 0 | 0 | 0 | 0 |
|  | SL |  | 11 | 11,5 | 11,5 | 12 |

Table III-continued

| | Untreated | Treated with liquors | | | |
|---|---|---|---|---|---|
| | | A | B | C | D |
| Handle* after subsequent washing (*see Table I) | 0 | 3 | 2¼ | 2¼ | 2¾ |

What is claimed is:

1. A phosphorus-containing condesation products made from
    a. 2 to 6 moles of an amidophosphate of the formula

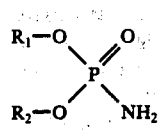

in which $R_1$ and $R_2$ each independently are alkyl having 1 to 4 carbon atoms, halogenoalkyl or alkenyl having 2 to 4 carbon atoms, or $R_1$ and $R_2$ together are alkylene having 2 to 4 carbon atoms;
    b. 1 mole of a 1,3,5-triazine substituted by at least 2 primary amino groups;
    c. 2 to 12 moles of formaldehyde or of an agent releasing formaldehyde; and optionally
    d. 0 to 6 moles of an alkanol having 1 to 4 carbon atoms.

2. Phosphorus-containing condensation products according to claim 1 obtained by a process in which the constituents (a), (b) and (c) are all reacted simultaneously; or firstly (a) is reacted with (c) and afterwards with (b); or firstly (b) is reacted with (c) and afterwards with (a); or firstly (b) is reacted with (c), thereupon with (a) and subsequently again with (c).

3. A phosphorus-containing condensation products according to claim 1 which product is made from 2 to 6 moles of constituent (a), 1 mole of the constituent (b), 2 to 6 moles of the constituent (c) and 0 to 5 moles of the constituent (d), with the procedure being such that constituents (a), (b) and (c) are all reacted simultaneously, or firstly (a) is reacted with (c) and afterwards with (b), or firstly (b) is reacted with (c) and afterwards with (a).

4. A phosphorus-containing condensation products according to claim 1, which product is made by reacting together 2 to 5 moles of the constituent (a), 1 mole of the constituent (b), 3 to 5 moles of the constituent (c) and 0 to 3 moles of the constituent (d).

5. A phosphorus-containing condensation products according to claim 1, which product is made from the component (a) and a methylolated 1,3,5-aminotriazine substituted by at least 2 primary amino groups.

6. A phosphorus-containing condensation products according to claim 1, which product is made from a O,O'-dialkylamido-phosphate as constituent (a) corresponding to one of the formulae

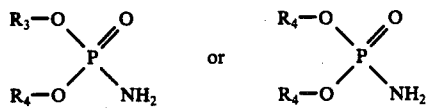

in which $R_3$ and $R_4$ each are alkyl having 1 to 4 carbon atoms.

7. A phosphorus-containing condensation products according to claim 1, which product is made from a constituent (a) consisting of 2,2-dimethylcyclopropyl-O,O'-amidophosphate, di-isopropyl- or diethyl-O,O'-amidophosphate.

8. A phosphorus-containing condensation products according to claim 1, which product is made from a constituent (b) consisting of melamine.

9. A phosphorus-containing condensation products according to claim 1, which product is made from constituent (d) consisting of ethanol or methanol.

10. A phosphorus-containing condensation products according to claim 1, which product corresponds to the formula

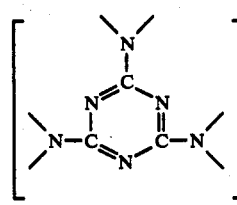
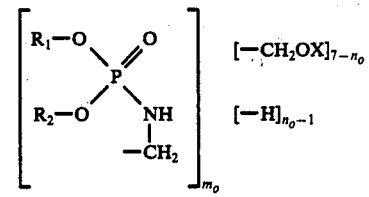

in which $R_1$ and $R_2$ have the meanings given in claim 1, X is hydrogen or alkyl having 1 to 4 carbon atoms, $m_o$ an integer from 2 to 6, and $n_o$ an integer from 1 to 7.

11. A phosphorus-containing condensation products according to claim 1, which product corresponds to the formula

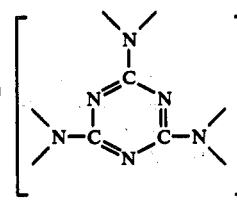
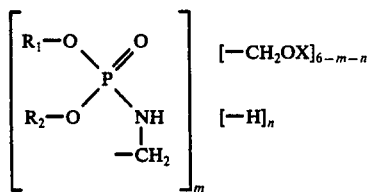

in which $R_1$ and $R_2$ have the meanings given in claim 1, X is hydrogen or alkyl having 1 to 4 carbon atoms, $m$ an integer from 2 to 6, and $n$ an integer of at most 6-$m$.

12. A phosphorus-containing condensation products according to claim 1, which product corresponds to the formula

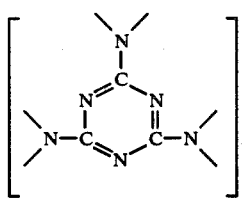

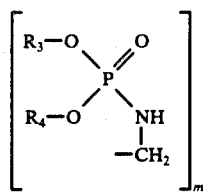 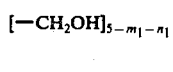

in which $R_3$ and $R_4$ each are alkyl having 1 to 4 carbon atoms, $m_1$ is an integer from 2 to 5, and $n_1$ an integer of at most $5-m_1$.

13. The phosphorus-containing condensation products according to claim 1, which product corresponds to the formula

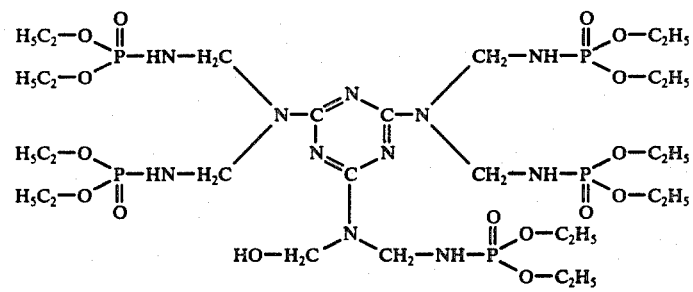

14. A process for the manufacture of a phosphorus-containing condensation products from an amidophosphate and an aminotriazine, in which process
 a. 2 to 6 moles of an amidophosphate of the formula

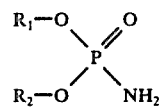

in which $R_1$ and $R_2$ each independently are alkyl having 1 to 4 carbon atoms, halogenoalkyl having 2 to 4 carbon atoms, alkenyl having 2 to 4 carbon atoms, or $R_1$ and $R_2$ together are alkylene having 2 to 4 carbon atoms,
 b. 1 mole of a 1,3,5-triazine substituted by at least two primary amino groups, and
 c. 2 to 12 moles of formaldehyde or of an agent releasing formaldehyde, are reacted together at a temperature of 70° to 180° C, and
 d. subsequently etherified with 0 to 6 moles of an alkanol having 1 to 4 carbon atoms.

15. Agent for the fireproofing of cellulose-containing fiber materials, which agent consists of an aqueous preparation containing a phosphorus-containing condensation products made from
 a. 2 to 6 moles of an amidophosphate of the formula

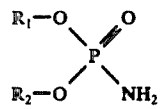

in which $R_1$ and $R_2$ each independently are alkyl having 1 to 4 carbon atoms, halogenoalkyl or alkenyl having 2 to 4 carbon atoms, or $R_1$ and $R_2$ together are alkylene having 2 to 4 carbon atoms;
 b. 1 mole of a 1,3,5-triazine substituted by at least 2 primary amino groups;
 c. 2 to 12 moles of formaldehyde or of an agent releasing formaldehyde; and
 d. 0 to 6 moles of an alkanol having 1 to 4 carbon atoms.

* * * * *